(12) United States Patent
Suga et al.

(10) Patent No.: US 6,533,771 B2
(45) Date of Patent: Mar. 18, 2003

(54) SANITARY TAMPON OF SMALL FIBER AGGLOMERATIONS

(75) Inventors: Ayami Suga, Kagawa (JP); Mitsuhiro Wada, Kagawa (JP)

(73) Assignee: Uni-Charm Corporation, Ehime (JP)

( * ) Notice: Subject to any disclaimer, the term of this patent is extended or adjusted under 35 U.S.C. 154(b) by 0 days.

(21) Appl. No.: 09/770,557

(22) Filed: Jan. 26, 2001

(65) Prior Publication Data

US 2001/0012929 A1 Aug. 9, 2001

(30) Foreign Application Priority Data

Feb. 2, 2000 (JP) ........................................ 2000-024663

(51) Int. Cl.$^7$ ............................. A61F 13/20; A61F 13/15
(52) U.S. Cl. ........................................ 604/904; 604/367
(58) Field of Search ........................... 604/904, 385.17, 604/385.18, 385.01, 367

(56) References Cited

U.S. PATENT DOCUMENTS

| | | | | |
|---|---|---|---|---|
| 3,815,601 A | * | 6/1974 | Schaefer | 604/15 |
| 4,058,124 A | * | 11/1977 | Yen et al. | 47/9 |
| 4,239,043 A | * | 12/1980 | Gellert | 428/313.5 |
| 4,278,088 A | * | 7/1981 | Reeves et al. | 128/270 |
| 4,341,215 A | * | 7/1982 | Eldridge | 604/368 |
| 4,543,098 A | * | 9/1985 | Wolfe et al. | 604/370 |
| 6,310,269 B1 | * | 10/2001 | Friese et al. | 28/118 |

FOREIGN PATENT DOCUMENTS

| | | |
|---|---|---|
| JP | 62-236547 | 10/1987 |
| JP | 1-146548 | 6/1989 |
| JP | 3-146058 | 6/1991 |
| JP | 05-068695 | 3/1993 |

* cited by examiner

*Primary Examiner*—Dennis Ruhl
*Assistant Examiner*—C L Anderson
(74) *Attorney, Agent, or Firm*—Darby & Darby

(57) ABSTRACT

Provided is a sanitary tampon including an absorbent wrapped by a liquid-pervious sheet. The absorbent is a mass of a plurality of compressed, small fiber agglomerations. At least the small fiber agglomerations located in the peripheral region of the absorbent are bonded to each other via hydrogen bonding therebetween.

14 Claims, 2 Drawing Sheets

SANITARY TAMPON OF SMALL FIBER AGGLOMERATIONS

BACKGROUND OF THE INVENTION

1. FIELD OF THE INVENTION

The present invention relates to a sanitary tampon which is inserted into a body cavity such as a woman's vagina to absorb menstrual fluid, blood and other kinds of body fluid.

2. DESCRIPTION OF THE RELATED ART

Recently, various types of sanitary tampons have been developed and put on the market. For example, Japanese Unexamined Patent Publication (Kokai) No. Heisei 1-146548 discloses a sanitary tampon that comprises an absorbent of hydrophilic fibers and an outer layer of a hydrophobic sheet mixed with hydrophilic fibers. Japanese Unexamined Patent Publication (Kokai) No. Heisei 3-146058 discloses a tampon that comprises a columnar, highly-compressed core and an outer envelope. Japanese Unexamined Patent Publication (Kokai) No. Heisei 5-68695 discloses a tampon which comprises a combination of sheets having a higher fiber density and sheets having a lower fiber density and is so constructed that, when formed into a columnar structure, the sheets having a lower fiber density are partly exposed outside the surface of the structure. These tampons have columnar structures of compressed absorbent fiber materials. While used, they absorb menstrual discharges, and are then uncompressed. As a result, the thus-uncompressed tampons expand to block the vaginal cavity, and can further absorb the menstrual discharges.

However, since these types of the tampons have such columnar structures formed by highly compressing integrated fibrous mats, they are problematic in that the fibrous mats constituting them are too rigid and are therefore hardly restored to their original, non-compressed size so as to well fit into the vagina, and that the menstrual discharges often leak outside through the inevitable space between an inner wall of the vagina and the tampon.

On the other hand, Japanese Unexamined Patent Publication (Kokai) No. Showa 62-236547 discloses a tampon comprising a plurality of small fiber agglomerations. In this tampon, the constituent fiber agglomerations have some space between them. Therefore, the tampon could be easily deformed, and could well fit into the vagina. However, since the fiber agglomerations constituting the tampon have some space between them, the fiber content of the tampon will reduce if the density of the fiber agglomerations is lowered so as to increase the absorption rate into the fiber agglomerations. If so, the absorbability of the tampon as a whole is thereby reduced. On the other hand, if the density of the fiber agglomerations is increased so as to increase the absorbability of the tampon, the absorption rate into the fiber agglomerations will lower. In addition, since the fiber agglomerations constituting the tampon have some space between them, the tampon itself is not rigid enough to easily insert the tampon into the vagina.

SUMMARY OF THE INVENTION

An object of the present invention is to provide a tampon which has high absorbability, and hardly forms a space between the tampon and an inner wall of the vagina.

According to one aspect of the invention, a sanitary tampon may comprise an absorbent wrapped by a liquid-pervious sheet, wherein;

the absorbent is a mass of a plurality of compressed, small fiber agglomerations, at least the small fiber agglomerations located in the peripheral region of the absorbent are bonded to each other via hydrogen bonding therebetween.

The absorbent of the sanitary tampon of the invention is formed of a plurality of small fiber agglomerations bonded to each other. When the tampon has been inserted into the vagina and brought into contact with a small quantity of discharges therein, the hydrogen bonding between the small fiber agglomerations constituting the absorbent is broken and, as a result, the thus-broken fiber agglomerations exhibit their individual behavior. In that condition, the compressed fiber agglomerations are restored to their original, non-compressed size. Accordingly, the tampon in the vagina well fits to the inner wall of the vagina with no space between the tampon and the inner wall of the vagina. In addition, since the small fiber agglomerations constituting the absorbent of the tampon are tightly compressed and since at least the small fiber agglomerations located in the peripheral region of the absorbent are bonded to each other via hydrogen bonding therebetween, the tampon is rigid by itself and is easy to insert into the vagina.

The density of the small fiber agglomerations located in the center region of the absorbent of the tampon may be higher than that of the small fiber agglomerations located in the peripheral region thereof. In the tampon of this embodiment, since the density of the small fiber agglomerations located in the peripheral region of the absorbent is lower than that of the others, the small fiber agglomerations located in the peripheral region can rapidly absorb discharges to break the hydrogen bonding between them, whereby the absorbent shall have a freedom of behavior as a whole. As a result, the small fiber agglomerations having a higher density and located in the center region of the absorbent can behave relatively freely. The small fiber agglomeration having a higher density can expand to a higher degree when having absorbed discharges, and, as a result, the absorbent well expands to facilitate fitting in the vagina.

The small fiber agglomerations located in the center region of the absorbent may be formed of noncellulosic fibers alone or of a combination of cellulosic fibers and noncellulosic fibers, and those located in the peripheral region thereof may be formed of cellulosic fibers alone or of a combination of cellulosic fibers and noncellulosic fibers; and the small fiber agglomerations located in the center region of the absorbent may contain a larger quantity of noncellulosic fibers than those located in the peripheral region thereof. In such a tampon, the small fiber agglomerations located in the center region of the absorbent are essentially formed of noncellulosic fibers. Therefore, the elastic recovery of this tampon is high. When the small fiber agglomerations essentially formed of cellulosic fibers in the peripheral region of the absorbent of the tampon have absorbed discharges to break the hydrogen bonding between them, the absorbent is rapidly expanded owing to the expansion force of the small fiber agglomerations located in the center region of the absorbent.

If desired, the respective small fiber agglomerations may be of a core/shell structure, and the density of the core of each fiber agglomeration is higher than that of the shell.

Also if desired, the core of the small fiber agglomeration is formed of noncellulosic fibers alone or of a combination of cellulosic fibers and noncellulosic fibers; and the shell thereof is formed of cellulosic fibers alone or of a combination of cellulosic fibers and noncellulosic fibers, and the core contains a larger quantity of noncellulosic fibers than the shell.

Preferably, in the tampon of the invention; the small fiber agglomerations constituting the absorbent may contain both cellulosic fibers and noncellulosic fibers in a blend ratio of cellulosic fibers to noncellulosic fibers falling between 0.5:1 and 4:1.

Also preferably, the mean fiber density of the absorbent falls between 0.2 and 0.9 g/cm$^3$.

According to another aspect of the invention, a sanitary tampon-may comprise an absorbent wrapped by a liquid-pervious sheet, wherein;

the absorbent includes a web of compressed and hydrogen-bonded fibers; and a plurality of small fiber agglomerations contained in the web, and the small fiber agglomerations are compressed to have a higher density than the web.

According to still another aspect of the invention, a sanitary tampon may comprise an absorbent wrapped by a liquid-pervious sheet, wherein;

the absorbent includes a web of compressed and hydrogen-bonded cellulosic fibers alone or of a combination of cellulosic fibers and noncellulosic fibers all compressed and hydrogen-bonded; and a plurality of small fiber agglomerations of noncellulosic fibers alone or of a combination of cellulosic fibers and noncellulosic fibers to be contained in the web, and the non-cellulosic fiber content of the small fiber agglomerations is higher than that of the web.

In these tampons of the invention, the fibrous web rapidly absorbs discharges to break the hydrogen bonding of the fibers constituting it, whereby the absorbent gets a freedom of behavior. In that condition, the small fiber agglomerations having a higher density in the fibrous web, or those therein containing noncellulosic fibers and therefore having an increased degree of elastic recovery expand to a great extent, and, as a result, the absorbent well expands to facilitate fitting in the vagina.

In the tampons of the invention, it is desirable that the small fiber agglomerations are formed by winding up fibers. More preferably, the small fiber agglomerations of high-density fibers or those of noncellulosic fibers therein are formed by winding up the fibers, so that their expansion recovery becomes large when they have absorbed discharges.

DESCRIPTION OF THE PREFERRED EMBODIMENTS

Figure 1:
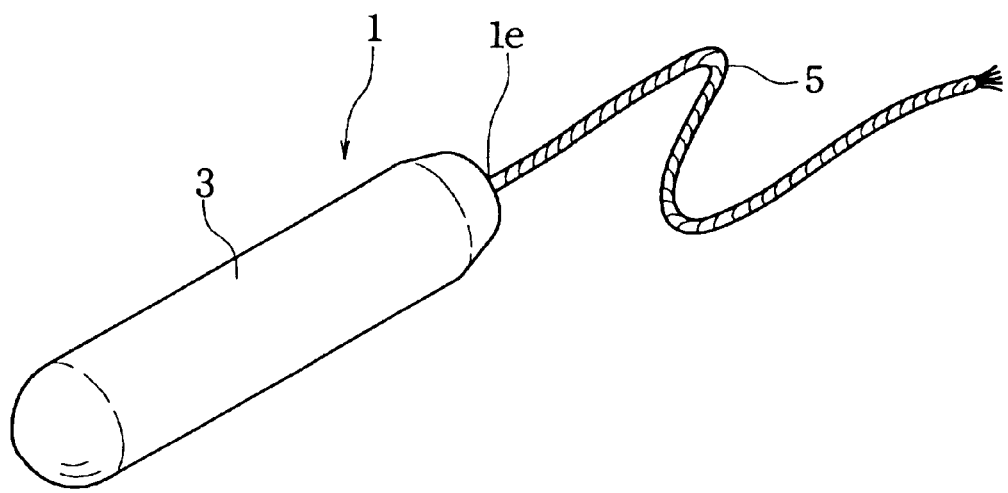
FIG. 1 is a perspective view of one embodiment of a tampon according to the invention.

The invention will be described with reference to the accompanying drawings. FIG. 1 is a perspective view of one embodiment of a tampon according to the invention; and FIG. 2 is a partial cross-sectional view of the tampon of FIG. 1.

Figure 2:
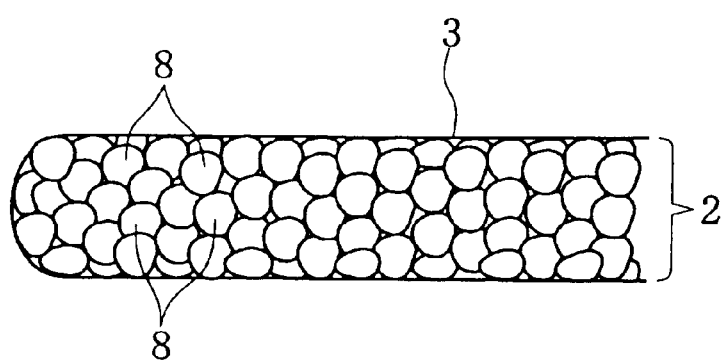
FIG. 2 is a partial cross-sectional view of the tampon of FIG. 1.

A tampon 1 shown in FIG. 1 is so constructed that a columnar, compression-shaped absorbent 2 as shown in FIG. 2 is covered with a liquid-pervious sheet 3. At a rear end 1e of the tampon 1, the liquid-pervious sheet 3 is heat-sealed or sewed on a machine. The tampon 1 is provided with a string 5 extending from the rear end 1e of the tampon 1 for taking the tampon out of the vagina by pulling the string 5 after used.

The liquid-pervious sheet 3 may be made of a spun-lace, point-bonded, spun-bonded or thermal-bonded non-woven fabric of hydrophilicated hydrophobic fibers of polyester, polypropylene or polyethylene terephthalate, etc., or of such a non-woven fabric having been perforated to have a number of perforations therethrough, or even of a porous plastic sheet or the like. One preferred example of the sheet is a spun-bonded non-woven fabric of polyester having a unit weight (Metsuke) of 12 g/m$^2$ or so. The string 5 may be made of any materials. For example, it may be a cotton yarn (of 16 cotton fibers of count # 20) having been processed for water repellency.

As shown in FIG. 2, the absorbent 2 is made of a mass of a plurality of small fiber agglomerations 8, and the mass is shaped under compression into a columnar structure having, for example, a diameter of from 8 to 20 mm or so and a length of from 4 to 7 cm or so. In this, the small fiber agglomerations 8 are tightly bonded to each other. At least the small fiber agglomerations located in the peripheral region of the absorbent 2 contain cellulosic fibers, and the neighboring fiber agglomerations located at least in the peripheral region are bonded to each other via hydrogen bonding therebetween. However, all the small fiber agglomerations as-shown in FIG. 2 may be bonded to each other via hydrogen bonding therebetween.

The respective small fiber agglomerations 8 are formed by winding up fibers having a length of from 10 to 40 mm or so into spirals or balls, followed by compressing them. The thus-formed fiber agglomerations 8 are enveloped in the liquid-pervious sheet 3. Having been thus enveloped in the sheet, the columnar mass of the fiber agglomerations has a size capable of well fitting in the vagina. The small fiber agglomerations 8 thus enveloped in the liquid-pervious sheet 3 are then compressed under heat to form a columnar structure having a diameter of from 8 to 20 mm or so and a length of from 4 to 7 cm or so. While being compressed under heat in this step, at least the small fiber agglomerations 8 located in the peripheral region of the columnar structure (but preferably all the small fiber agglomerations 8 constituting the columnar structure) are bonded to each other via hydrogen bonding therebetween. Preferably, the weight of one fiber agglomeration 8 falls between 1 and 3 g or so.

Since the thus-compressed small fiber agglomerations 8 are bonded to each other via hydrogen bonding therebetween, the absorbent 2 composed of them becomes rigid and its self-retention becomes high. Accordingly, the tampon is easily inserted into the vagina. Even when it is inserted into the vagina by use of a tampon applicator, it can be readily pushed out of the tampon applicator with retaining the shape thereof.

After the tampon has been inserted into the vagina and have absorbed menstrual discharges therein, the hydrogen bonding of the neighboring fiber agglomerations 8 that constitute the tampon is broken, and, as a result, the individual fiber agglomerations can exhibit its free behavior. In that condition, therefore, the tampon can more readily fit in the vagina. In addition, the individual fiber agglomerations 8 having absorbed menstrual discharges are restored to their original, non-compressed condition, and, as a result, the absorbent 2 well expands as a whole to have little space from an inner wall of the vagina, and therefore prevents the leakage of menstrual discharges through it.

After shaped under compression, the absorbent 2 preferably has a mean density of from 0.2 to 0.9 g/m$^3$.

Also preferably, the small fiber agglomerations 8 constituting the absorbent 2 are wound up into spirals or balls, since the force of the fibers being unwound and restored could enhance the restoration of the fiber agglomerations to their original condition (i.e., the restoration referred to herein means both the rate and the force of restoration).

Concretely, the fibers to form the small fiber agglomerations 8 may be absorbent natural fibers alone, such as cellulosic rayon fibers, pulp fibers, cotton fibers or the like, or may be such cellulosic fibers combined with noncellulosic synthetic fibers such as polyethylene fibers, polypropylene fibers, polyethylene terephthalate fibers, etc. Essentially comprising such cellulosic fibers, the small fiber agglomerations 8 can be readily bonded to each other via hydrogen bonding therebetween. In addition, when the small fiber agglomerations 8 contain noncellulosic fibers having a high modulus of elasticity (elastic recovery), the individual fiber agglomerations 8 could ensure higher restorative expansion after having been released from the hydrogen bonding between them and having become relatively free for their individual behavior.

In order that the small fiber agglomerations 8 are well bonded to each other via hydrogen bonding therebetween to ensure the rigidity of the absorbent 2 comprising them and retain the columnar shape thereof, but that they can be well restored to their original, non-compressed condition after having been released from the hydrogen bonding between them, it is desirable that the blend ratio (by mass) of the cellulosic fibers to the noncellulosic fibers to form the columnar absorbent 2 falls between 0.5:1 and 4:1. Also preferably, the cellulosic fibers and the noncellulosic fibers are uniformly mixed to form the small fiber agglomerations. If desired, the noncellulosic fibers constituting the small fiber agglomerations 8 may be processed for hydrophilication.

Preferred examples of the small fiber agglomerations 8 are those formed by winding up 3.3 dtex rayon fibers having, for example, a length of 32 mm into small balls each having an outer diameter of 5 mm and a weight of 2 g; and those formed by mixing 80% by mass of 3.3 dtex rayon fibers having, for example, a length of 32 mm with 20% by mass of 6.6 dtex polyester fibers having, for example, a length of 38 mm, followed by winding up the resulting fiber mixture into small balls each having an outer diameter of 5 mm.

Figure 3:
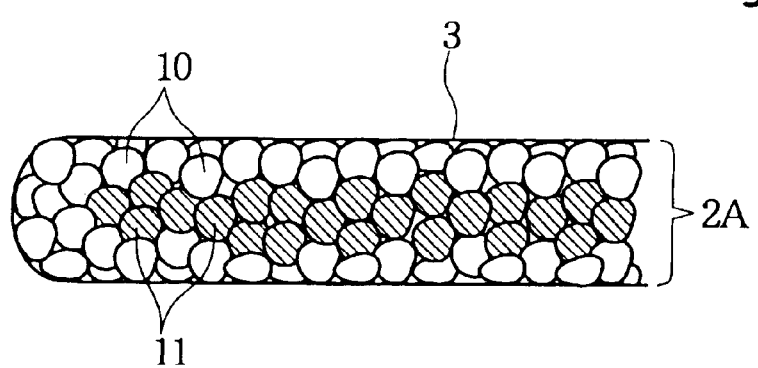
FIG. 3 is a partial cross-sectional view of another embodiment of the tampon according to the invention.

In the illustrated embodiment of FIG. 2, the plurality of small fiber agglomerations 8 constituting the absorbent 2 all have nearly the same density; but in the illustrated embodiment of FIG. 3, small fiber agglomerations 11 located in the center region of an absorbent 2A (these are hatched as shown in FIG. 3) have a higher density than the small fiber agglomerations 10 located in the peripheral region of the absorbent 2A.

As is the case with the small fiber agglomerations 8 constituting the absorbent 2, the small agglomerations 10 and 11 constituting the absorbent 2A are formed of cellulosic fibers, or are formed of a combination of cellulosic fibers and noncellulosic fibers. The absorbent 2A of FIG. 3 differs from the absorbent 2 of FIG. 2 in that the density of the fiber agglomerations 10 differs from that of the fiber agglomerations 11.

In the absorbent 2A of FIG. 3, the low-density fiber agglomerations 10 constituting the peripheral region immediately absorb menstrual discharges, and the thus absorbed discharges are then led to the high-density center region. Therefore, the absorbent 2A can more rapidly absorb menstrual discharges. After the fiber agglomerations 10 and 11 have thus absorbed menstrual discharges, their hydrogen bonding is broken, and, as a result, the agglomerations 10 and 11 can be relatively free for their individual behavior. In that condition, since the expansion recovery of the high-density fiber agglomerations 11 in the center region is larger, the absorbent 2A can well expand as a whole, and, as a result, the discharge absorbability of the tampon in itself increases and the tampon 1 can well fit in the vagina.

All the small fiber agglomerations 10 in the peripheral region of the absorbent, 2A and the small fiber agglomerations 11 in the center region thereof may be formed of a combination of cellulosic fibers and noncellulosic fibers; and the noncellulosic fiber content of the small fiber agglomerations 11 in the center region may be larger than that of the small fiber agglomerations 10 in the peripheral region. On the other hand, the small fiber agglomerations 10 in the peripheral region may be formed of cellulosic fibers alone, and the small fiber agglomerations 11 in the center region may be formed of a combination of cellulosic fibers and noncellulosic fibers; or the small fiber agglomerations 10 in the peripheral region may be formed of cellulosic fibers alone, and the small fiber agglomerations 11 in the center region may be formed of noncellulosic fibers alone. In these embodiments, the small fiber agglomerations 10 in the peripheral region are essentially bonded to each other via hydrogen bonding therebetween. In such embodiments of the absorbent 2A in which the small fiber agglomerations 10 and 11 differ in the cellulosic fiber content and the noncellulosic fiber content, the density of the agglomerations 11 is not always required to be higher than that of the agglomerations 10.

In the absorbent 2A, the small fiber agglomerations 10 of essentially cellulosic fibers in the peripheral region can rapidly absorb menstrual discharges. With that, after the hydrogen bonding between the agglomerations 10 thus having absorbed menstrual discharges has been broken, the agglomerations 11 of essentially noncellulosic fibers having high elastic recovery in the center region well expand owing to their high elastic recovery. Accordingly, when having absorbed menstrual discharges, the tampon well expands as a whole and ensures smooth bulk recovery. Cellulosic fibers can be readily bonded to each other via hydrogen bonding therebetween. Therefore, if containing a large quantity of such cellulosic fibers in its peripheral region, the absorbent 2A can readily retain the shape thereof as shown in FIG. 1. Accordingly, the absorbent 2A is rigid and is hardly deformed. As a result, the absorbent 2A is easy to insert into the vagina. When the applicator is used for it, the absorbent 2A is readily pushed out of the applicator.

One preferred example of the small fiber agglomerations 11 to be located in the center region of the absorbent is prepare by mixing 3.3 dtex rayon fibers having a length of 32 mm with 6.6 dtex polyester fibers having a length of 38 mm in a ratio of 50% to 50%, followed by forming the resulting fiber mixture into agglomerations each having an outer diameter of 5 mm. On the other hand, the small fiber agglomerations 10 to be located in the peripheral region of the absorbent may be formed of 3.3 dtex rayon fibers having a length of 32 mm, alone, and each has-an outer diameter of 5 mm.

Figure 4:
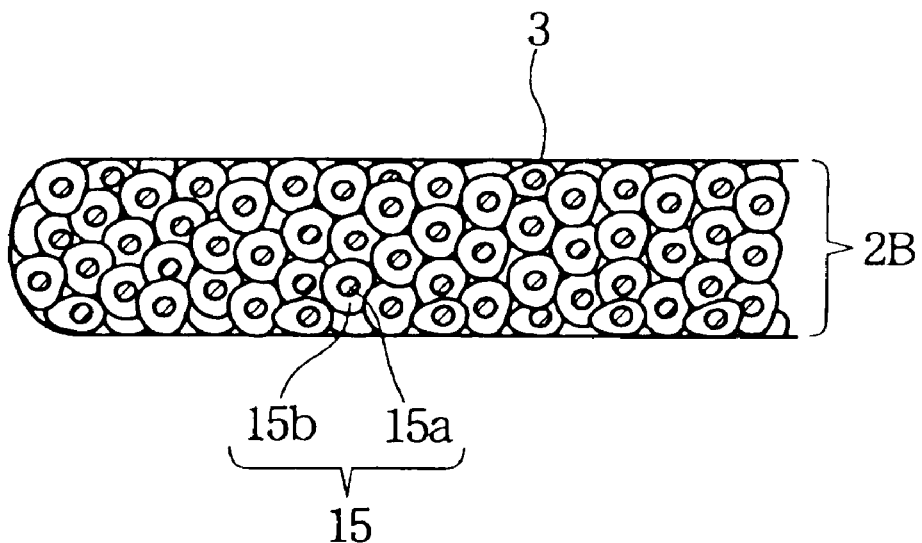
FIG. 4 is a partial cross-sectional view of still another embodiment of the tampon according to the invention.

FIG. 4 is a partial cross-sectional view of still another embodiment of the tampon of the invention.

As shown in FIG. 4, the respective small fiber agglomerations 15 constituting the absorbent 2B are composed of a core 15a (hatched portion) and a shell 15b that surrounds the core 15a (i.e., the small fiber agglomeration is of a core/shell structure). The core 15a and the shell 15b are both formed of cellulosic fibers alone, or may be formed of a combination of cellulosic fibers and noncellulosic fibers uniformly mixed in a ratio by mass falling between 0.5:1 and 4:1. In this embodiment, however, the fiber density of the core 15a is higher than that of the shell 15b.

The individual small fiber agglomerations 15 in this embodiment rapidly absorb menstrual discharges at the shell 15b, and the thus-absorbed discharges are then immediately led to the core 15a. When the shells 15b have absorbed menstrual discharges, the hydrogen bonding between the fiber agglomerations 15 is broken, and, as a result, the thus-released fiber agglomerations could be relatively free for their individual behavior. In this condition, the cores 15a having a higher density are well restored to their original condition. Therefore, when having absorbed menstrual discharges, the individual fiber agglomerations 15 ensures good bulk recovery and, as a result, the absorbent 2B well expands as a whole to thereby surely block the space between the inner wall of the vagina.

Both the core 15a and the shell 15b constituting each small fiber agglomeration 15 may be formed of a mixture of cellulosic fibers and noncellulosic fibers; and the noncellulosic fiber content of the core 15a may be larger than that of the shell 15b. The shell 15b maybe formed of cellulosic fibers alone, and the core 15a may be formed of noncellulosic fibers alone, or of a mixture of noncellulosic fibers and cellulosic fibers. In this case, the fiber density of the core 15a is not always required to be higher than that of the shell 15b. For these, it is desirable that the core 15a and the shell 15b are formed by winding up the fibers.

In the absorbent 2B, since the shell 15b of each small fiber agglomeration 15 is essentially formed of cellulosic fibers, the individual fiber agglomerations 15 can rapidly absorb menstrual discharges. After the hydrogen bonding between the fiber agglomerations 15 having thus absorbed discharges has been broken and the thus-released agglomerations 15 have become relatively free for their individual behavior, the noncellulosic fibers essentially constituting the core 15a and having high elastic recovery could be readily unwound, and the individual fiber agglomerations 15 will well restore to their original, noncompressed condition. In that condition, the absorbent 2B well expands to fit in the vagina. In addition, a large quantity of cellulosic fibers capable of being readily bonded to each other via hydrogen bonding therebetween exist in the surface of each fiber agglomeration in the absorbent 2B. Therefore, when the absorbent 2B is shaped under compression, the fiber agglomerations constituting it can be surely bonded to each other via hydrogen bonding therebetween to thereby enhance the self-retention of the compressed absorbent 2B.

For the tampon of the invention to be formed of a plurality of the small fiber agglomerations, the agglomerations 10, 11 and 15 may be combined in any desired manner. For example, the fiber agglomerations 15 of FIG. 4 may be used for the fiber agglomerations in the peripheral region of the absorbent 2A of FIG. 3 or for those in the center region of the absorbent 2A of FIG. 3. In the absorbent 2B of FIG. 4, the density of the small fiber agglomerations in the center region may be made higher than that of the small fiber agglomerations in the peripheral region; or the noncellulosic fiber content of the cores 15a of the small fiber agglomerations in the center region may be made higher than that of the cores 15a of the small fiber agglomerations in the peripheral region.

Figure 5:
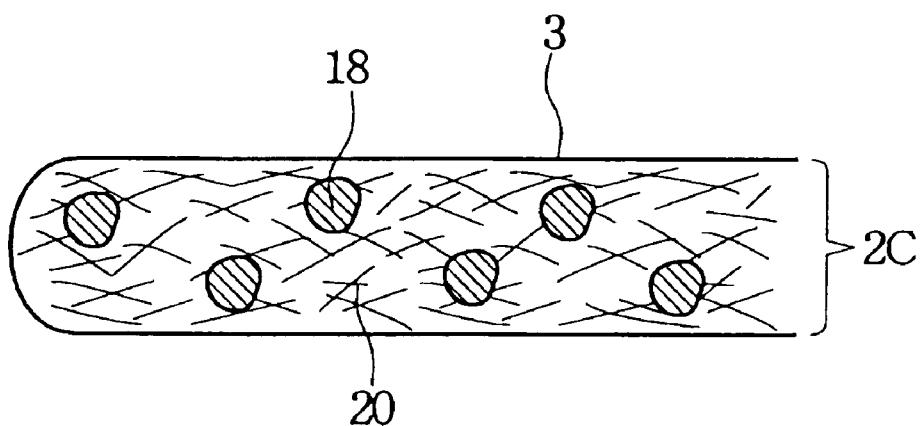
FIG. 5 is a partial cross-sectional view of still further embodiment of the tampon according to the invention.

FIG. 5 is a partial cross-sectional view of still further embodiment of the tampon of the invention.

As shown in FIG. 5, the absorbent 2C of the tampon is formed of a fibrous web 20 with a plurality of small fiber agglomerations 18 being spot-wise in the fibrous web 20. As the case may be, the small fiber agglomerations 18 may be concentrated in the center region of the fibrous web 20. The fibrous web 20 comprises cellulosic fibers, in which the fibers are, as being compressed under heat, bonded to each other via hydrogen bonding therebetween. The fibrous web 20 may be formed of cellulosic fibers alone, or of a mixture of cellulosic fibers and noncellulosic fibers. Since the fibers constituting the fibrous web 20 are bonded to each other via hydrogen bonding therebetween, the absorbent 2C is rigid and is hardly deformed. Therefore, the absorbent 2C is easy to insert into the vagina. When the applicator is used for it, the absorbent 2C is readily pushed out of the applicator.

The small fiber agglomerations 18 are formed of cellulosic fibers alone or of a mixture of cellulosic fibers and noncellulosic fibers. Preferably, they are formed by winding up the fibers. The fiber density of the agglomerations 18 is higher than that of the fibrous web 20. Since the fibrous web 20 having such a relatively low fiber density forms the surface of the absorbent 2C, the absorbent 2C ensures rapid absorption of menstrual discharges. After having been absorbed by the fibrous web 20, the menstrual discharges are readily led to the fiber agglomerations 18 having a higher density. in that manner, the menstrual discharges having been absorbed by, the fibrous web 20 can readily move into the inside of the absorbent 2C. After the fibrous web 20 has absorbed discharges and the hydrogen bonding between the fibers constituting the fibrous web 2C has been broken, the absorbent 20C gets a freedom for its behavior and can smoothly deform to fit in the vagina. When the high-density fiber agglomerations 18 in the absorbent 2C have absorbed discharges, they well expand to be well restored to their original, non-compressed condition. Accordingly, the absorbent 2C containing the agglomerations 18 also well expands to be bulky and facilitates fitting in the vagina, when having absorbed discharges.

In the illustrated embodiment of FIG. 5, all the fibrous web 20 and the small fiber agglomerations 18 may be formed of a mixture of cellulosic fibers and noncellulosic fibers, and the noncellulosic fiber content of the fiber agglomerations 18 may be higher than that of the fibrous web 20. On the other hand, the fibrous web 20 may be formed of a mixture of cellulose fibers and noncellulosic fibers, and the small fiber agglomerations 18 may be formed of noncellulosic fibers alone; or the fibrous web 20 may be formed of cellulosic fibers alone, and the small fiber agglomerations 18 may be formed of a mixture of cellulosic fibers and noncellulosic fibers or of noncellulosic fibers alone.

In this embodiment, when the hydrogen bonding in the fibrous web 20 is broken, the small fiber agglomerations 18 well expand owing to the elastic recovery of the noncellulosic fibers constituting them, and, as a result, the absorbent 2C thereby well expands as a whole.

The small fiber agglomerations 18 in this embodiment may be the same as the fiber agglomerations 15 shown in FIG. 4.

To produce the absorbent 2C of FIG. 5, for example, the small fiber agglomerations 18 are put on the flat fibrous web 20, and the fibrous web 20 with the fiber agglomerations 18 thereon is shaped under compression into a columnar structure; or a fibrous web 20 containing the small fiber agglomerations 18 therein is firstly shaped into a columnar structure and then the columnar structure is compressed under heat.

As set forth above, the tampon of the invention is so constituted that the hydrogen bonding of the small fiber agglomerations constituting it is broken when the tampon has absorbed the menstrual discharges, and the thus-released fiber agglomerations can exhibit their individual behavior. Therefore, when inserted into the vagina, the tampon well fits therein, not forming space from the inner wall of the vagina, and the menstrual discharges do not leak out therethrough.

When the density of the small fiber agglomerations located in the center region of the tampon is increased, the menstrual discharges having been absorbed by the tampon can be readily led to the center region of the absorbent. Therefore, the tampon of the illustrated embodiment can rapidly absorb the menstrual discharges, and can rapidly expand to fit in the vagina. In addition, not only the surface of the absorbent but also the inside thereof is effectively utilized for absorbing discharges. Further, when the center region of the tampon is formed of small fiber agglomerations containing a large quantity of noncellulosic fibers, the bulk recovery of the tampon having absorbed the menstrual discharges is increased. Therefore, the tampon of the illustrated embodiment facilitates fitting in the vagina, not forming a space from the inner wall of the vagina.

When the density of the cores of the small fiber agglomerations constituting the tampon is made higher than that of the shells thereof, the discharge absorbability of the individual fiber agglomerations is increased. Further, when the cores of the small fiber agglomerations contain a large quantity of noncellulosic fibers, the bulk recovery of the fiber agglomerations is increased. Therefore, the tampon facilitates fitting in the vagina, not forming a space from the inner wall of the vagina.

When the absorbent of the tampon is formed of the fibrous web with high-density fiber agglomerations being spot-wise in the fibrous web, the discharge absorability of the tampon is increased, and the elastic recovery thereof is also increased.

While the invention has been described in detail and with reference to specific embodiments thereof, it will be apparent to one skilled in the art that various changes and modifications can be made therein without departing from the spirit and scope thereof.

What is claimed is:

1. A sanitary tampon comprising an absorbent wrapped by a liquid-pervious sheet, wherein;
    the absorbent is a mass of a plurality of compressed, small fiber agglomerations formed by winding fibers into spirals and balls which are then compressed, at least the small fiber agglomerations located in a peripheral region of the absorbent are bonded to each other via hydrogen bonding therebetween.

2. The sanitary tampon as set forth in claim 1, wherein a fiber of the small fiber agglomerations has a length of from 10 to 40 mm.

3. The sanitary tampon as set forth in claim 1, wherein a weight of one fiber agglomeration is in a range of 1 and 3 g.

4. A sanitary tampon comprising an absorbent wrapped by a liquid-pervious sheet, wherein;
    the absorbent includes a web of compressed and hydrogen-bonded fibers; and a plurality of compressed small fiber agglomerations formed by winding fibers into spirals and balls which are then compressed, the small fiber agglomerations having a higher density than the web.

5. The sanitary tampon as set forth in claim 4, wherein the absorbent includes a web of compressed and hydrogen-bonded cellulosic fibers alone or of a combination of cellulose fibers and noncellulosic fibers all compressed and hydrogen-bonded; and a plurality of small fiber agglomerations of noncellulosic fibers which are formed by winding fibers into spiral balls which are then compressed or of a combination of cellulosic fibers and noncellulosic fibers to be contained in the web, and the noncellulosic fiber content of the small fiber agglomerations is higher than that of the web.

6. The sanitary tampon as set forth in claim 4, wherein a fiber of the small fiber agglomerations has a length of from 10 to 40 mm.

7. The sanitary tampon as set forth in claim 4, wherein a weight of one fiber agglomeration is in a range of 1 and 3 g.

8. A sanitary tampon comprising an absorbent wrapped by a liquid-pervious sheet, wherein;
    the absorbent is a mass of a plurality of compressed, small fiber agglomerations formed by winding fibers into spirals and balls which are then compressed, at least the small fiber agglomerations located in a peripheral region of the absorbent are bonded to each other via hydrogen bonding therebetween, and wherein;
    a density of the small fiber agglomerations located in a center region of the absorbent is higher than that of the small fiber agglomerations located in the peripheral region thereof.

9. The sanitary tampon as set forth in claim 8, wherein the small fiber agglomerations located in the center region of the absorbent are formed of noncellulosic fibers alone or of a combination of cellulosic fibers and noncellulosic fibers; and the small fiber agglomerations located in the peripheral region of the absorbent are formed of cellulosic fibers alone or of a combination of cellulosic fibers and noncellulosic fibers, and the small fiber agglomerations located in the center region of the absorbent contain a larger quantity of noncellulosic fibers than those located in the peripheral region thereof.

10. The sanitary tampon as set forth in claim 8, wherein each of the small fiber agglomerations is of a core/shell structure, and the density of a core of the small fiber agglomeration is higher than that of a shell thereof.

11. The sanitary tampon as set forth in claim 10, wherein the core of the small fiber agglomeration is formed of noncellulosic fibers alone or of a combination of cellulosic fibers and noncellulosic fibers; and the shell thereof is formed of cellulosic fibers alone or of a combination of cellulosic fibers and noncellulosic fibers, and the core contains a larger quantity of noncellulosic fibers than the shell.

12. The sanitary tampon as set forth in claim 11, wherein the small fiber agglomerations contain both cellulosic fibers and noncellulosic fibers in a blend ratio of cellulosic fibers to noncellulosic fibers falling between 0.5:1 and 4:1.

13. The sanitary tampon as set forth in claim 8, wherein a mean fiber density of the absorbent is in a range of between 0.2 and 0.9 g/cm$^3$.

14. A sanitary tampon comprising an absorbent wrapped by a liquid-pervious sheet, wherein;
    the absorbent is a mass of a plurality of compressed, small fiber agglomerations formed by winding fibers into spirals and balls which are then compressed, at least the small fiber agglomerations located in a peripheral region of the absorbent are bonded to each other via hydrogen bonding therebetween, and wherein;
    each of the small fiber agglomerations is of a core/shell structure, and a density of the core of the small fiber agglomeration is higher than that of the shell thereof.

* * * * *